United States Patent
Cash

(10) Patent No.: US 9,561,199 B2
(45) Date of Patent: *Feb. 7, 2017

(54) ACTIVATION OF AMP-PROTEIN ACTIVATED KINASE BY OXALOACETATE COMPOUNDS

(71) Applicant: Alan B Cash, San Diego, CA (US)

(72) Inventor: Alan B Cash, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/707,063

(22) Filed: May 8, 2015

(65) Prior Publication Data

US 2015/0238450 A1 Aug. 27, 2015

Related U.S. Application Data

(62) Division of application No. 13/806,465, filed as application No. PCT/US2011/041377 on Jun. 22, 2011, now Pat. No. 9,050,306.

(60) Provisional application No. 61/357,263, filed on Jun. 22, 2010.

(51) Int. Cl.
| | | |
|---|---|---|
| *A61K 31/194* | (2006.01) | |
| *A61K 31/155* | (2006.01) | |
| *A61K 31/375* | (2006.01) | |
| *A61K 31/4439* | (2006.01) | |
| *A61K 31/198* | (2006.01) | |
| *A61K 31/427* | (2006.01) | |
| *A61K 45/06* | (2006.01) | |

(52) U.S. Cl.
CPC .......... *A61K 31/194* (2013.01); *A61K 31/155* (2013.01); *A61K 31/198* (2013.01); *A61K 31/375* (2013.01); *A61K 31/427* (2013.01); *A61K 31/4439* (2013.01); *A61K 45/06* (2013.01)

(58) Field of Classification Search
IPC ............. A61K 31/194,31/4439, 31/155, 31/375
See application file for complete search history.

(56) References Cited

U.S. PATENT DOCUMENTS

| | | | |
|---|---|---|---|
| 5,914,326 A | 6/1999 | McCarty et al. | |
| 7,078,396 B2 * | 7/2006 | Song | A61K 31/045 514/182 |
| 2006/0281691 A1 | 12/2006 | Blass | |
| 2008/0057088 A1 * | 3/2008 | Blass | A61K 8/0208 424/401 |
| 2008/0279786 A1 | 11/2008 | Cash | |
| 2010/0104548 A1 * | 4/2010 | Rossetti | A61K 31/198 424/94.4 |

FOREIGN PATENT DOCUMENTS

WO  WO 2006/087759  *  8/2006

OTHER PUBLICATIONS

Cash (Open Longevity Science, 2009, 3, 22-27.*
Kumler et al., (J. Org. Chem (1962; 27(4), 1165-1167).
Bartley Biochem J. (1995); 59(2): 194-202.
Delchev (J. Structural Chemistry, 48(4), 615-622, (2007).
Cash, "Oxaloacetic Acid Supplementation as a Mimic of Calorie Restriction," Open Longevity Science, 2009, vol. 3, pp. 22-27.
International Search Report issued in PCT/2011/041377 dated Feb. 29, 2012.

* cited by examiner

*Primary Examiner* — Shirley V Gembeh
(74) *Attorney, Agent, or Firm* — Sughrue Mion, PLLC

(57) ABSTRACT

The present invention relates to oxaloacetate compounds that activate AMP-activated protein kinase (AMPK), including the preparation of the compounds, compositions containing the compounds, preserving said compounds and the use of the compounds in the prevention or treatment of disorders such as diabetes, metabolic syndrome, obesity, cardiovascular disease, Alzheimer's disease, and cancer.

19 Claims, No Drawings

ACTIVATION OF AMP-PROTEIN ACTIVATED KINASE BY OXALOACETATE COMPOUNDS

This is a divisional of Application Ser. No. 13/806,465 filed Feb. 19, 2013, which is a 35 U.S.C. §371 National Stage application of International Application No. PCT/US2011/041377 filed Jun. 22, 2011, claiming priority based on U.S. Provisional Application No. 61/357,263 filed Jun. 22, 2010, the contents of all of which are incorporated herein by reference in their entirety.

BACKGROUND OF THE INVENTION

AMP-protein activated Kinase (AMPK) is a sensor and regulator of cellular energy homeostasis, is a master switch regulating glucose and lipid metabolism and activation of AMPK results in many beneficial effects. (Misra, et al, The role of AMP kinase in diabetes, Indian J Med Res 125:389-398 (2007); Kola, et al, The Role of AMP-Activated Protein Kinase in Obesity, Obesity and Metabolism, Vol 36 (2008); Kahn, et al, AMP-activated protein kinase: ancient energy gauge provides clues to modern understanding of metabolism. Cell Metab. 1(10:15-25 (2005); Hardie, D. G. and Hawley, S. A. AMP-activated protein kinase: the energy charge hypothesis revisited. Bioessays 23: 1112 (2001), Kemp, B. E. et.al. AMP-activated protein kinase, super metabolic regulator. Biochem. Soc. Transactions 31:162 (2003)). AMPK can be activated by three distinct mechanisms; 1) allosteric activation, 2) stimulation of phosphorylation of the alpha-subunit on Thr172 by upstream kinase(s), and 3) inhibition of dephosphorylation by protein phosphatases (Kola, et al, The Role of AMP-Activated Protein Kinase in Obesity. Obesity and Metabolism 36:198-211 (2008)). The resulting activation leads to a decrease in fatty acid synthesis and oxidation, and a decrease in cholesterol synthesis (Carling, D. et.al. A common bicyclic protein kinase cascade inactivates the regulatory enzymes of fatty acid and cholesterol biosynthesis. FEBS Letters 223:217 (1987)). Other effects of AMPK activation include positive changes in the levels of potential drug targets for components of the metabolic syndrome including hormone sensitive lipase, glycerol-3-phosphate acyltransferase, malonyl-CoA decarboxylase, and hepatocyte nuclear factor-4.alpha. AMPK activation stimulates glucose transport in skeletal muscle and controls expressional regulation of key genes in fatty acid and glucose metabolism in liver (summarized in U.S. patent application Ser. No. 7,119,205).

Genomic pathways that AMPK activation affects include decreased expression of glucose-6-phosphatase (a key enzyme in hepatic glucose production) (Lochhead, P. A. et.al. 5-aminoimidazole-4-carboxamide riboside mimics the effects of insulin on the expression of the 2 key gluconeogenic genes PEPCK and glucose-6-phosphatase. Diabetes 49:896 (2000)), and SREBP-1c (Zhou, G. et.al. Role of AMP-activated protein kinase in mechanism of metformin action. The J. of Clin. Invest. 108: 1167 (2001)), a key lipogenic transcription factor. Note that the metabolic changes induced by AMPK activation are both acute changes due to phosphorylation of key enzymes, and longer-term effects on the expression of genes involved in metabolic regulation.

There have been several studies that indicate that activation of AMPK will result in many benefits. In the liver, there is decreased glucose output and improvement in glucose homeostasis, decreased fatty acid and cholesterol synthesis and increased fatty acid oxidation. In skeletal muscle tissue there is increased glucose uptake and fatty acid oxidation. There is a reduction in intra-myocyte triglyceride accumulation and improved insulin action. A reduction in the ability to store fat, due to the down-regulation of fatty acid synthesis, results in long-term weight reductions. The combinations of all these effects are an excellent treatment for metabolic syndrome, diabetes and obesity.

Several studies in rodents and humans support that AMPK activation leads to substantial benefits (Bergeron, R. et.al. Effect of 5-aminoimidazole-4-carboxamide-1(beta)-D-ribofuranoside infusion on in vivo glucose metabolism in lean and obese Zucker rats. Diabetes 50:1076 (2001), Song, S. M. et.al. 5-Aminoimidazole-4-darboxamide ribonucleoside treatment improves glucose homeostasis in insulin-resistant diabeted (ob/ob) mice. Diabetologia 45:56 (2002), Halseth, A. E. et.al. Acute and chronic treatment of ob/ob and db/db mice with AICAR decreases blood glucose concentrations. Biochem. and Biophys. Res. Comm. 294:798 (2002), Buhl, E. S. et.al. Long-term AICAR administration reduces metabolic disturbances and lowers blood pressure in rats displaying feature of the insulin resistance syndrome. Diabetes 51: 2199 (2002)). Activation of AMPK increases mitochondrial biogenesis (Reznick, et al, The role of AMP-activated protein kinase in mitochondrial biogeneses. J Physiol 574.1 (2006)). Reduced mitochondria content is important in the pathogenesis of insulin resistance and type 2 diabetes.

Many in vivo studies have relied on the AMPK activator 5-Aminoimidazole-4-darboxamide ribonucleoside (AICAR), a cell permeable precursor of ZMP. ZMP acts as an intracellular AMP mimic, and, when accumulated to high enough levels, is able to stimulate AMPK activity (Corton, J. M. et.al. 5-Aminoimidazole-4-carboxamide ribonucleoside, a specific method for activating AMP-activated protein kinase in intact cells? Eur. J. Biochem. 229: 558 (1995)). Several in vivo studies have demonstrated beneficial effects of both acute and chronic AICAR administration in rodent models of obesity and type 2 diabetes (Bergeron, R. et.al. Effect of 5-aminoimidazole-4-carboxamide-1(beta)-D-ribofuranoside infusion on in vivo glucose metabolism in lean and obese Zucker rats. Diabetes 50:1076 (2001), Song, S. M. et.al. 5-Aminoimidazole-4-darboxamide ribonucleoside treatment improves glucose homeostasis in insulin-resistant diabeted (ob/ob) mice. Diabetologia 45:56 (2002), Halseth, A. E. et.al. Acute and chronic treatment of ob/ob and db/db mice with AICAR decreases blood glucose concentrations. Biochem. and Biophys. Res. Comm. 294:798 (2002), Buhl, E. S. et.al. Long-term AICAR administration reduces metabolic disturbances and lowers blood pressure in rats displaying feature of the insulin resistance syndrome. Diabetes 51: 2199 (2002)). For example, 7 week AICAR administration in the obese Zucker (fa/fa) rat leads to a reduction in plasma triglycerides and free fatty acids, an increase in HDL cholesterol, and a normalization of glucose metabolism as assessed by an oral glucose tolerance test (Minokoshi, Y. et.al. Leptin stimulates fatty-acid oxidation by activating AMP-activated protein kinase. Nature 415: 339 (2002)). In both ob/ob and db/db mice, 8 day AICAR administration reduces blood glucose by 35% (Halseth, A. E. et.al. Acute and chronic treatment of ob/ob and db/db mice with AICAR decreases blood glucose concentrations. Biochem. and Biophys. Res. Comm. 294:798 (2002)). In addition to AICAR, more recently it was found that the diabetes drug metformin can activate AMPK in vivo at high concentrations (Zhou, G. et.al. Role of AMP-activated protein kinase in mechanism of metformin action. The J. of Clin. Invest. 108: 1167 (2001), Musi, N. et.al. Metformin increases AMP-activated protein kinase activity in skeletal muscle of subjects with type 2 diabetes. Diabetes 51: 2074 (2002)).

In addition to pharmacologic intervention, several transgenic mouse models have been developed in the last years, and initial results are becoming available. Expression of dominant negative AMPK in skeletal muscle of transgenic mice has demonstrated that the AICAR effect on stimulation of glucose transport is dependent on AMPK activation (Mu, J. et.al. A role for AMP-activated protein kinase in contraction and hypoxia-regulated glucose transport in skeletal muscle. Molecular Cell 7: 1085 (2001)).

Lowering of blood pressure has been reported to be a consequence of AMPK activation (Buhl, E. S. et.al. Long-term AICAR administration reduces metabolic disturbances and lowers blood pressure in rats displaying feature of the insulin resistance syndrome. Diabetes 51: 2199 (2002)), therefore activation of AMPK has beneficial effects in hypertension. Through combination of some or all of the above-mentioned effects stimulation of AMPK is expected to reduce the incidence of cardiovascular diseases (e.g. MI, stroke). Endothelial NO synthase (eNOS) has been shown to be activated through AMPK mediated phosphorylation (Chen, Z.-P., et.al. AMP-activated protein kinase phosphorylation of endothelial NO synthase. FEBS Letters 443: 285 (1999)), therefore AMPK activation by any means can be used to improve local circulatory systems.

Increased fatty acid synthesis is a characteristic of many tumor cells, therefore decreased synthesis of fatty acids through activation of AMPK can be useful as a cancer therapy. Cell cultures exposed to AICAR to activate AMPK attenuated the growth of MDA-MB-231 tumors in nude mice (Swinnen, JV, et al. Mimicry of a Cellular Low Energy Status Blocks Tumor Cell Anabolism and Suppresses the Malignant Phenotype. Cancer Res 2005; 65:6 (2005)). The AMPK activator metformin inhibits breast cancer cells, pancreatic cancer (Zakikhani, et. at, Metformin is an AMP-Kinase-Dependent Growth Inhibitor for Breast Cancer Cells. Cancer Research 66, 10269-10273 (2006), (Schhneider, et. al, Metformin clearly inhibits pancreatic cancer. Cancer Detection and Prevention Online, Abstract 260 (2002)) and reduces overall cancer risk (Evans, et al, Metformin and reduced risk of cancer in diabetic patients. BMJ 330:1304-1305 (2005)). Resveratrol also activates AMPK to kill cancer cells (Hwang, et. al. Resveratrol Induces Apoptosis in Chemoresistant Cancer Cells via Modulation of AMPK Signaling Pathway. Annals of the New York Academy of Sciences, V 1095 Signal Transduction Pathways, Part C: Cell Signaling in Health and Disease, 441-448 (2007)).

There are several current methods to activate AMPK, but these methods have some problems associated with them. As stated above, AMPK can be activated with metformin, resveratrol and AICAR. But metformin may also produce lactic acidosis, which can become a life-threatening condition, especially where a patient has renal insufficiency. Still further, metformin therapy is often counter-indicated where a patient takes other drugs that interfere with renal function. Resveratrol has a very low bioavailability, and large amounts may be necessary in order to achieve efficacy. AICAR is banned by the World Anti-Doping Code for athletic events (The Prohibited List 2009, World Anti-Doping Agency, http://www.wada-ama.org/rtecontent/document/2009_Prohibited_List_ENG_Final_20_Sept_08.pdf), and is currently not available for human use.

Other methods to activate AMPK include diabetic drug class thiazolidinediones (LeBrasseur, et al, Thiazolidinediones can rapidly activate AMP-activated protein kinase (AMPK) in mammalian tissues. Am J Physiol Endocrinol Metab (2006) and (Matejkova, et al, Possible involvement of AMP-activated protein kinase in obesity resistance induced by respiratory uncoupling in white fat. FEBS Letters, 539 (1-3):245-248 (2003)). However, various thiazolidinediones have been withdrawn from the market or development has discontinued due to relatively high hepatotoxicity. (Isley, Hepatotoxicity of thiazolidinediones. Expert Opinion on Drug Safety, 2(6):581-586 (2003)). Recently, overstimulation of PPAR gamma has also been implicated in increased chances of developing colorectal cancer. The withdrawal of troglitazone has led to concerns of the other thiazolidinediones also increasing the incidence of hepatitis and potential liver failure, an approximately 1 in 20,000 individual occurrence with troglitazone. Because of this, the FDA recommends two to three month checks of liver enzymes for the first year of thiazolidinedione therapy to check for this rare but potentially catastrophic complication. In addition, thiazolidinediones have a side effect of water retention, leading to edema. Recent studies have shown there may be an increased risk of coronary heart disease and heart attacks with the thiazolidinedione rosiglitazone (Clinical Trials for Rosiglitazone, www.ClinicalTrials.gov).

The reduction of calories below baseline ad. Librium feeding levels (Calorie Restriction) is one method to induce AMPK activation. The extension of lifespan in the nematode worm Caenorhabditis elegans are shown to be completely dependent on the activation (phosphorylation) of AMP-protein activated kinase (AMPK) and the FOXO transcription factor DAF-16 (Greer, et al, An AMPK-FOXO pathway mediates longevity induced by a novel method of dietary restriction in C. elegans. Current Biology 9:17(19):1646-56 (2007)). Under Calorie Restriction, cellular energy depletion causes rising AMP levels, and an increase in the Nicotinamide Adenine Dinucleotide (NAD+) level as compared to the reduced level (NADH), results in activation of AMPK (Raphaloff-Phail, et al Biochemical regulation of mammalian AMP-activated protein kinase (AMPK) activity by NAD and NADH. Journal of Biological Chemistry, Manuscript M409574200 (2004)). While Calorie Restriction is a low-risk method to activate AMPK, it requires the reduction of baseline food consumption to levels that are not desirable to the majority of the population due to extreme hunger. The diet is extremely difficult to follow over time.

Strenuous exercise can also activate AMPK (Lee-Young, et al "AMPK activation is fiber type specific in human skeletal muscle: effects of exercise and short-term exercise training, Journal of Applied Physiology, 2009 July; 107(1); 283-9) however, again, this may not be desirable or achievable by the majority of the population.

In animal models, various stresses such as oxidative stress, hypoxia, ischemia and heat shock can activate AMPK (Towler, et. al, AMP-activated protein kinase in metabolic control and insulin signaling Circ Res. 100, 328-341 (2007). These stresses are not recommended as an AMPK activation agent.

Undoubtedly, activation of AMPK can aid in the prevention or treatment of disorders such as diabetes, metabolic syndrome, obesity, cardiovascular disease, dyslipidemia and cancer. Current activation of AMPK which includes strenuous exercise, calorie restriction, pharmacological interventions mimetics metformin and resveratrol, and thiazolidinediones all have side effects which are detrimental or difficult to implement over time. Therefore, there exists a need in the market for an AMPK activator which has high bioavailability, low toxicity, and preferably is already a human metabolite which would lower overall pharmacological risk. The currently proposed invention meets those needs.

SUMMARY OF THE INVENTION

In CR a low energy state produces signaling events to affect expression levels of genes involved with cellular proliferation, apoptosis, electron transport chain, immune response, protein turnover and protein synthesis (Lee C K, Pugh T D, Klopp R G, et al. The impact of alpha-lipoic acid, coenzyme Q10 and caloric restriction on life span and gene expression patterns in mice. Free Radic Biol Med 2004;36: 1043-57.). Identifying these signaling events that produce the CR metabolic state has generated the search for CR mimetics, that is, compounds that invoke this state and produce the benefits of CR without actually requiring a reduction in caloric intake (Lane M A, Ingram D K, Roth G S. The serious search for an anti-aging pill. Sci Am 2002; 287:36-41.; also Ingram D K, Roth G S, Lane M A, et al. The potential for dietary restriction to increase longevity in humans: extrapolation from monkey studies. Biogerontology 2006;7:143-8.). Interestingly, it appears there are multiple longevity pathways that can be activated in CR, depending on how CR is implemented (Greer, et al, An AMPK-FOXO pathway mediates longevity induced by a novel method of dietary restriction in *C. elegans*. Current Biology 9:17(19):1646-56 (2007)). One such pathway, based on activating AMP-activated protein kinase (AMPK) and a functional transcription factor FOXO/DAF-16, has been directly tied to CR in *C. elegans* (Greer, et al, An AMPK-FOXO pathway mediates longevity induced by a novel method of dietary restriction in *C. elegans*. Current Biology 9:17(19):1646-56 (2007)). AMPK has also been shown to be activated under CR in animal models (Pallottini V, Montanari L, Cavallini G, Bergamini E, Gori Z, Trentalance A. Mechanisms underlying the impaired regulation of 3-hydroxy-3-methylglutaryl coenzyme A reductase in aged rat liver. Mech Ageing Dev 2004;125:633-9; also Greer, et al, An AMPK-FOXO pathway mediates longevity induced by a novel method of dietary restriction in *C. elegans*. Current Biology 9:17(19):1646-56 (2007)). Both AMPK and FOXO/DAF-16 are conserved homologs throughout the animal kingdom, giving rise to the opportunity to use CR mimetics to activate AMPK as one of the CR pathways and receive the benefits of AMPK activation in mammals, including humans.

Previously, I discovered that oxaloacetic acid, its salts and precursors such as alpha-ketoglutarate and aspartate ("OAA" as a group) can act as CR mimentics (Cash, U.S. patent application Ser. No. 11/792,703 filed May 13, 2008, which is a 371 of PCT/US05/46130 filed Dec. 15, 2005, claiming benefit of U.S. Provisional Application 60/637,287 filed Dec. 17, 2004). I discovered that supplementation of the CR mimetic, OAA, activates AMPK and allows for the multiple benefits of AMPK activation, which is discussed herein.

AMPK is a heterotrimeric complex that consists of a catalytic alpha subunit and regulatory beta and gamma subunits that together make a functional enzyme, conserved from yeast to humans. The alpha AMPK subunit is activated in order to increase lifespan (Apfeld, et al, The AMP-activated protein kinase AAK-2 links energy levels and insulin-like signals to lifespan in *C. elegans*. Genes and Development 18:3004-3009 (2004)). This same AMPK activation for lifespan extension has been shown to be the same mechanism as CR for lifespan extension (Greer, et al, An AMPK-FOXO pathway mediates longevity induced by a novel method of dietary restriction in *C. elegans*. Current Biology 9:17(19):1646-56 (2007)).

I have assayed the CR mimetic OAA for AMPK activation by using the worm *C. elegans* containing a non-functional alpha AMPK subunit, and have compared lifespan with and without the functional AMPK subunit. CR mimetics will increase the lifespan of *C. elegans* in worms with functional FOXO/DAF-16 and AMPK by 25%, p<0.001, but will not increase the lifespan of the worms with a non-functional alpha AMPK subunit. Graph 1 is the Kaplan-Meyer survival curves for worms with functional and non-functional AMPK showing the difference in lifespan. The graphs clearly show that OAA increases lifespan in the worms with functional AMPK but do not increase lifespan in the worms with non-functional AMPK. This clearly indicates that the CR mimetic OAA increases AMPK activation. Further, wild type worms with functional AMPK that are subjected to calorie restriction do not have their lifespan increased with OAA supplementation, indicating that AMPK activation is a component of the CR pathway.

With AMPK activation, there will be a reduction in the incidence, and beneficial treatment of a variety of conditions including type 2 diabetes, Alzheimer's disease, metabolic syndrome, obesity, cardiovascular disease, dyslipidemia, stroke and cancer.

I have investigated the toxicity of OAA in an acute study and two chronic studies. The acute study showed a LD50 of more than 5,000 mg OAA/Kg of mouse (when taken with food), generally considered to be the regulatory threshold for "non-toxic" compounds. The first chronic study, performed with 380 mg OAA/kg of mouse, performed over eighteen months with older mice, indicate a "negative" toxicity, as the mice on OAA lived 25% longer than the control group. In the second test, performed with rats over 90 days, indicated no observed adverse effect level (NOAEL) of 500 mg OAA/kg of rat, the highest dose given in the study. As human dosage for effective treatment is in the range of 50 mg to 2,000 mg, more preferably from 100 mg to 1,000 mg, and most preferably from 100 mg to 300 mg, per day, for a 70 kg person this is only a dosage of 1.4 to 4.2 mg OAA/kg human. OAA shows a tolerance safety factor of 100× or more for treatment and prevention. This should not be surprising, as OAA is a key metabolite found in every human cell.

Thus, according to one embodiment of the present invention there is provided a method of preventing and treating method of treating diabetes in a mammal, comprising administration of a therapeutically effective amount of OAA to activate AMPK.

In another embodiment of the present invention, there is provided a pharmaceutical composition which includes a pharmaceutically acceptable carrier in combination with OAA, effective to modulate glucose metabolism in a mammal when the composition is administered to the mammal at a concentration effective to modulate glucose metabolism.

Furthermore, it should be noted that contemplated pharmaceutical compositions may additionally include a second pharmaceutical agent, and most preferably a pharmaceutical agent for treatment of type-2 diabetes, metabolic syndrome, pre-diabetes, and dyslipidemia. Thus, suitable second pharmaceutical agents include various biguanides, sulfonyl ureas, meglitinides, thiazolidinediones, and additional compounds used for treatment.

In addition to contemplated pharmaceutical compositions for the treatment of type-2 diatetes, metabolic syndrome, pre-diabetes and dyslipidemia, compositions with OAA may include nutritional supplements that are agents to treat these conditions, which include, but are not limited to, caffeine, cinnamon, cinnamon extracts, oregano, *Euonymus alatus*, non-toxic chromium salts, *Gymnema sylvestre*, Alpha lipoic acid, Vanadyl sulfate, Biotin, B-complex vitamins, Vitamin C, Magnesium salts and Magnesium stearate, resveratrol, CoQ10, Vitamin E, Banaba leaf, *Thymus vulgaris* extract, Pancreas extract, Adrenal extract, DHEA, Psyllium, *Panax ginseng, Momordica charantia, Allium sativum, Vaccinium myrtillus, Trigonella foenum*-gracecum, *Gingko biloba, Oenothera biennis*, peppermint, chamomile, passionflower, Corosolic acid, Pine Bark Extract (Proanthocyanidins).

In another aspect of the inventive subject matter, a method of modulating glucose metabolism in a mammal includes a step of administering OAA at a dosage effective to modulate glucose metabolism in the mammal, wherein the mammal is preferably diagnosed with at least one of metabolic syndrome, pre-diabetes, type-2 diabetes and dyslipidemia. While not wishing to be bound by any specific theory or hypothesis, the inventors contemplate that the compounds according to the inventive subject matter will modulate the glucose metabolism by increasing AMPK activation through the use of OAA, and that such activation will modulate the glucose metabolism by increasing glucose uptake in a muscle cell, and/or decreasing gluconeogenesis in a hepatocyte, along with stimulating the up-regulation of the FOXO3a gene associated with glucose homeostasis.

In yet another aspect of the inventive subject matter, the inventor contemplates a method of treating a condition in a mammal associated with dysregulation of AMPK, wherein the method comprises a step of administering one or more of contemplated compounds at a dosage effective to activate AMPK, wherein the method comprises a step of administering OAA at a dosage effective to activate AMPK. Among other diseases, conditions associated with AMPK dysregulation include cardiovascular diseases, type 2 diabetes, and neoplastic diseases.

According to an additional embodiment of the present invention there is provided a method of preventing and treating Alzheimer's disease in a mammal, comprising administration of a therapeutically effective amount of OAA to activate AMPK.

According to an additional embodiment of the present invention there is provided a method of preventing and treating metabolic syndrome in a mammal, comprising administration of a therapeutically effective amount of OAA to activate AMPK.

According to an additional embodiment of the present invention there is provided a method of preventing and treating obesity in a mammal, comprising administration of a therapeutically effective amount of OAA to activate AMPK.

According to an additional embodiment of the present invention, there is provided a method of maintaining fat from re-accumulating after a diet, comprising administration of a therapeutically effective amount of OAA to activate AMPK.

According to an additional embodiment of the present invention, there is provided a method of preventing and treating cardiovascular disease in a mammal, comprising administration of a therapeutically effective amount of OAA to activate AMPK.

According to an additional embodiment of the present invention, there is provided a method of preventing and treating cancer, comprising administration of a therapeutically effective amount of OAA to activate AMPK.

According to an additional embodiment of the present invention, there is provided a method of increasing mitochondrial density, comprising administration of a therapeutically effective amount of OAA to activate AMPK.

According to an additional embodiment of the present invention there is provided a pharmaceutical composition comprising a therapeutically effective amount of OAA in combination with a pharmaceutically suitable carrier to activate AMPK.

As set forth herein, the invention includes administering a therapeutically effective amount of OAA and prodrugs thereof to a mammal. Preferably, the invention also includes administering a therapeutically effective amount of any OAA to a human to activate AMPK, and more preferably to a human in need of being treated for or prophylactically treated for any of the respective disorders set forth herein.

It is noted that the prevention and/or treatment of the disorders with OAA relates specifically to the activation of AMPK. The same disorders may be treated with the calorie restriction mimetic OAA may be treated through other pathways, which are covered in Cash, U.S. patent application Ser. No. 11/792,703 filed May 13, 2008, which is a 371 of PCT/US05/46130 filed Dec. 15, 2005, claiming benefit of U.S. Provisional Application 60/637,287 filed Dec. 17, 2004, incorporated herein by reference.

Stability of Oxaloacetic acid, oxaloacetate and oxaloacetate salts

Oxaloacetic acid (as opposed to OAA, previously defined as oxaloacetic acid, salts of oxaloacetic acid, metabolic precursors of oxaloacetic acid including alpha-ketoglutarate and aspartate and the oxaloacetate ion) when dissolved in water ionizes to oxaloacetate. The oxaloacetate can be in three forms depending on the pH of the solution. At low pH (<1.5) and low temperature (<4 degrees C.) oxaloacetate hydrates. At higher pH, oxaloacetic acid in water occurs in three forms, 1) the hydrated form, 2) a keto form, and 3) an enol form. Outside of water solutions, the solid form of oxaloacetic acid is primarily in the enol form. All forms of oxaloacetic acid and the ion oxaloacetate are absorbed by the body. The hydrated form is mostly converted once it enters the higher pH of the body outside of the intestinal tract to the keto and enol form. As a specific example, at a pH of 6.9, oxaloacetic acid in water is composed of 5% in the hydrated form, 84% in the keto form and 11% in the enol form. Enol-oxaloacetate is convert to keto-oxaloacetate with the enzyme enol-keto tautomerase, a ubiquitous enzyme throughout the human body.

While oxaloacetic acid can be given in any of the three forms and be effective (because the forms change with different pH conditions and enzymatic activity), there is a significant problem with stability that has prevented the commercialization of the compound as a therapeutic agent. Keto-oxaloacetic acid decarboxylates spontaneously into pyruvate and carbon dioxide, and neither byproduct of the decomposition is effective in activating AMPK. The stability problems of oxaloacetic acid are well documented in the literature (Krebs, H A, "The effect of inorganic salts on the ketone decomposition of oxaloacetic acid", Biochem J. 1942, April; 36(3-4):303-5; also Ochoa, S. "Biosynthesis of tricarboxylic acids by carbon dioxide fixation; the preparation and properties of oxalosuccinic acid", J Biol Chem 1948 May; 174(1):115-22; also Lynen, F and Scherer, H. Ann. Chem. 560, 163(1948); also Kosicki, et al, "Lithium Chloride Catalyzed Decarboxylation of Oxalacetic Acid in Ethanol", Canadian Journal of Chemistry, Vol 42 (1964); also Kosicki and Lipovac, "The pH and pD Dependence of the Spontaneous and Magnesium-ion-Catalyzed Decarboxylation of Oxalacetic Acid", Canadian Journal of Chemistry, Vol 42 (1964); also Bontchev and Michaylova, "Cataytic Activity and Complexation I, Influence of Organic Solvents on the Rate of Catalytic Decarboxylation of Oxalacetic Acid" J. Inorg. Nucl. Chem, 1967, Vol 29. Pp 2945 to 2953; also Kozlowske and Zuman, "Polarographic Reduction of Aldehyes and Ketones, Part XXX. Effects of Acid-Base, Hydration-Dehyration and Keto-enol Equilibria on Reduction of alpha-Ketoglutaric and Oxalacetic Acid and their Esters", J. Electroanal. Chem, 226 (1987) 69-102) and Speck, John, "The effect of Cations on the Decarboxylation of Oxalacetic Acid" J. Biological Chemistry, (1948)). The lack of stability of oxaloacetic acid has been a source of difficulty in the preparation of a commercial product. Yoshikawa (Yoshikawa, K, "Studies on Anti-diabetic Effect of Sodium Oxaloacetate", Tohoku J. Exp. Med, (1968) 96:127-141) teaches "Since oxaloacetic acid is unstable, its sodium salt was used in the animal experiment as well as in the clinical investigations" (page 128).

The enol and keto form of oxaloacetic acid are tautomers, and in water form a chemical equilibrium. At a pH of 6.9, oxaloacetic acid in water is composed of 5% in the hydrated form, 84% in the keto form and 11% in the enol form. The keto-oxaloacetate decarboxylates quickly to pyruvate. As the keto-oxaloacetate form disappears due to decarboxylation, the enol and hydrated form convert to keto-oxaloacetate, and then also decarboxylate into carbon dioxide and pyruvate, until all the oxaloacetate is consumed. Note that neither of the byproducts of oxaloacetate decarboxylation, carbon dioxide and pyruvate, are effective in activating AMPK. If there are divalent cations in the fluid, which is very common, the decarboxylation of oxaloacetic acid can happen within a day.

Salts of oxaloacetic acid, have been tested and are also not stable, despite the teachings of Yoshikawa. As a specific example of this, Na-OAA when dissolved in water will form 5% hydrated form, 84% in the keto form and 11% in the enol form, similar to oxaloacetic acid in water adjusted to a pH of 6.9. The keto-oxaloacetate decarboxylates quickly, followed by enol conversion to keto form and further decarboxylation. The sodium salt of oxaloacetic acid used in the Yoshikawa study must have been made up daily, which is not practical for a commercial product. Na-OAA has no shelf life, and is not available commercially.

The hydrated form of oxaloacetic acid can be made stable by maintaining it at very low pH, but only for less than one-week's time, at temperatures not exceeding 8 degrees C. Again, this does not allow commercial distribution of the product to persons needing prevention or therapy gained from oxaloacetic acid supplementation. The hydrated form of oxaloacetic acid has no shelf life.

Methods to Stabilize Oxaloacetic Acid, Oxaloacetate and Oxaloacetate Salts

In contrast with the multiple teachings of the literature, the current invention makes use of stable oxaloacetic acid in order to allow for a reasonable shelf life of one year or more. The stable oxaloacetic acid activates AMPK and achieves preventative and therapeutic effects. The invention uses anhydrous enol-oxaloacetic acid which is stable at room temperature for a period exceeding one year. The enol-oxaloacetic acid does not decarboxylate spontaneously and is thus stable if kept dry. Water catalyzes the equilibrium reaction between enol-and keto oxaloacetic acid. Note that only the keto form of oxaloacetic acid decarboxylates into pyruvate and carbon dioxide spontaneously, not the enol-form. There is an energy gap between the enol and keto form which is bridged when the compounds are exposed to water, however, this same energy gap prevents the conversion of the enol to keto form when the product is kept dry. Once there is a conversion to the keto form, decarboxylation can spontaneously occur at temperatures above the freezing point of water. Thus, manufacturing oxaloacetate with a water content of less than 2% and keeping the oxaloacetic acid in a solid state and dry through the use of moisture sealants and/or moisture absorbents, creates the commercial shelf-stable enol-oxaloacetate form, even at room temperatures. Drying effectiveness can be increased by increasing the drying time, drying under vacuum, by using anhydrous washes of isopropyl alcohol or ethyl alcohol to absorb the remaining water (and then evaporating the alcohol), or by performing multiple washes with hexane or non-water soluble solvent to physically remove the water, typically after an alcohol wash. The non-water soluble solvent would then be evaporated off. The small amount of non-water soluble solvent wash remaining in the oxaloacetic acid is non-toxic and serves to repel water moisture from entering into the powder to further extend shelf life. Hexane is a residual solvent in many commercial food preparations including decaffeinated coffee, and is not toxic in small quantities. Alternatively, the final wash can be performed with liquefied propane, liquefied butane, ethyl acetate, ethane, carbon dioxide, or nitrous oxide to reduce the water content.

The reduced water content oxaloacetate form can allow for the use of the compound in commerce, as the shelf life of the product will exceed one year with less than 1% product decay at room temperatures. An example of the manufacture of oxaloacetic acid prior to the improved drying step can be seen in Bessman; "Preparation and Assay of Oxalacetic Acid"; Arch. Biochem., vol. 26, pp. 418-421, 1950, also in Heidelberger; "The Synthesis of Oxalacetic Acid-1-C14 and Orotic Acid-6-C14", Biochem. Prepn. 3, 59 (1953) pp 4704-4706.

In practice, the isolation of the oxaloacetate from water in the atmosphere can be easily achieved after encapsulation of the oxaloacetic acid by sealing the bottles or placing individual capsules in a plastic blister pack. Reducing the water content below 2%, and most preferably below 1% along with isolation from the atmosphere, will keep the oxaloacetate in the enol form, and will prevent decarboxylation. Additional measures to prevent decarboxylation include the use of desiccants in the container with the enol-oxaloacetate and the addition of 10% to 90% anhydrous ascorbic acid per weight of oxaloacetic acid, or more preferably 50% anhydrous ascorbic acid per weight of oxaloacetic acid. Ascorbic acid acts as an electron acceptor and reduces the rate of decarboxylation. Most preferably, the combination of adding anhydrous ascorbic acid, sealing the container, and using an enol-form oxaloacetic acid below a 1% moisture level combine to yield a shelf-life of the product at 30 degrees C. in excess of one year.

The present invention also describes the methods used to stabilize sodium oxaloactate (and other salts, solutions and buffered solutions of oxaloacetic acid). Stabilization can be achieved by a biphasic containment system. Sodium oxaloacetate for commercial use can be made by using the solid anhydrous enol-form and combining it with a solution of water plus sodium hydroxide (NaOH) or other basic solution when needed. This can be in the form of a container with two separate compartments, one that contains the basic solution, and one that contains the anhydrous enol-oxaloacetate separated by a breakable barrier. When sodium oxaloacetate (or other salt) is needed, the barrier between the basic solution and the anhydrous oxaloacetate is broken, and oxaloacetate salt is quickly formed in solution. The solubility of oxaloacetic acid in water is 100 mg/ml, allowing rapid digestion of the anhydrous enol-oxaloacetic acid. Specific applications of a biphasic containment system include a flexible capsule, such as a gel cap which can be compressed by hand or with teeth to break an inner seal between the sodium hydroxide solution and the solid anhydrate enol-oxaloacetate. Another specific application of a biphasic containment system includes an intravenous (IV) bag with two compartments, one with an IV fluid and the other with anhydrous enol-oxaloacetic acid separated by a breakable barrier. When needed, the breakable barrier is ruptured, and the two components are mixed. The IV fluid can be a buffered solution, a non-buffered solution, an acidic solution, a basic solution or a neutral solution. Yet another example of a biphasic containment system is to have two separate containers; one for the solid oxaloacetic acid, and one for the liquids. Two separate containers will allow the solid oxaloacetic acid to be placed in storage below 0 degrees C., while the liquid container is kept at a different temperature. Storing the dry oxaloacetic acid at −20 degrees C. will enable the use of commonly available commercial oxaloacetic acid, without the additional drying step of the preparation. Again when needed, the two containers are joined and mixed to yield the oxaloacetate salt solution. A list of the storage temperature of commercially available oxaloacetic acid is shown below:

in human cells, and the conversion of oxaloacetate to malate is very energetically favorable (the Gibbs Free Energy, delta G, is highly negative (−29.7) indicating the reaction is very favorable to proceed). As oxaloacetate is converted to malate, NADH is converted to NAD+. The resulting increase in the NAD+/NADH ratio leads to the phosphorylation (activation) of AMPK (Rafaeloff-Phail R, Ding L, Conner L, et al. "Biochemical regulation of mammalian AMP-activated protein Kinase activity by NAD and NADH". *J Biol Chem* 2004; 279: 52934-9). AMPK serves to stimulate glucose uptake into the skeltal tissues and thereby reduces glucose levels. The immediate reduction is best seen with a glucose tolerance test in individuals that have defective leptin signaling (including overweight and obese persons) that are fasting. In these individuals, the defective leptin signaling which no longer activates AMPK is corrected by the oxaloacetic acid supplementation and the resulting increase in the NAD+/NADH ratio and activation of AMPK. Additionally, older individuals have reduced uptake of glucose into their muscle tissues, even if they are of a lean body type. AMPK activation can measureably improve glucose levels and glucose stability with these people.

In addition to improvements in glucose levels and reduction in insulin resistance, continuing supplementation of oxaloacetic acid supplementation and subsequent chronic

| Grade | Assay | Supplier | Storage temperature | Catalog No. |
|---|---|---|---|---|
| Oxaloacetic acid, puriss. | 98.0-101.0% | Reanal Private Ltd. | below 10° C. | 25380 |
| Oxalacetic acid | >=98.0% | Research Organics Inc. | −10--25° C. | 05130 |
| Oxalacetic acid | >=98.0% | Chem-Impex International | below 0° C. | 01460 |
| Oxalacetic Acid 98-99% | 98% | MP Biomedicals | 0° C. | 100568 |
| Oxalacetic Acid Cell Culture Reagent, 98-99% | 98% | MP Biomedicals | 0° C. | 194719 |
| Oxalacetic Acid | >95% | Wako Pure Chemical Industries | 2-10° C. | 15-0041 |
| Oxalacetic acid | ≥98% | Biosynth AG | −15° C. | O-5000 |
| Oxaloacetic acid | 97.5%-102.5% | Sigma-Aldrich Corp. | −20° C. | Aldrich 171255 |
| Oxaloacetic acid ~98% | ≥98% | Sigma Aldrich Corp. | −20° C. | Sigma O4126 |
| Oxaloacetic acid BioChemika | ≥98.0% | Sigma Aldrich Corp. | 2-8° C. | Fluka 75660 |
| Oxaloacetic acid, Hybri-Max ™ powder, hybridoma tested | ≥97.5% | Sigma Aldrich Corp. | −20° C. | Sigma O9504 |
| Oxaloacetic acid, insect cell culture tested | ≥97% | Sigma-Aldrich Corp. | −20° C. | Sigma O7753 |

Oxaloacetic Acid Effects in the Human Body

Humans that orally consume the solid oxaloacetic acid show reductions in blood glucose levels, due in part to activation of AMPK. The oxaloacetic acid is converted to the ionic form oxaloactate in the digestive tract, and is then absorbed into the body and is distributed throughout the body via the bloodstream. Yoshikawa measured the rate of oxaloacetate distribution into the bloodstream after 200 mg of sodium oxaloacetate was given to normal and diabetic patients. At time 0, the amount detected was 0 ug/100 ml blood, at time 30 minutes 0 ug/100 ml blood, and at time 60 minutes ranged from 1.5 to 3.1 mg/ 100 ml blood. My studies indicate that most of the oxaloacetic acid orally consumed is moved from the blood stream and taken into individual cells within 120 minutes. Within the cells the oxaloacetate reacts into L-malate as it encounters the enzyme malate dehydrogenase (MDH). MDH is ubiquitous NAD+/NADH ratio increase and further chronic activation of AMPK results in genomic changes. AMPK is part of a signaling cascade that influences which genes express proteins, and the amount of the expression. AMPK activation with the calorie restriction mimetic OAA over a period of 2.5 weeks is sufficient to see genomic changes in mice liver tissues using gene chips, and sufficient to see glucose related effects in all body types in humans. Gene changes documented in mice in my previous patent application include an increase in FOXO3a by 100 to 200%. FOXO3a is a gene that helps to regulate glucose levels. This increase in expression of FOXO3a requires functional AMPK. In diabetic patients, FOXO3a is downregulated, which results in glucose level instability.

Glucose related effects in humans have measured an 8 to 10% drop in fasting glucose levels in non-diabetic patients, a drop in triglyceride levels by 10% and a 55% reduction in the amplitude of fasting blood glucose levels. In diabetic patients, the effect is even more striking, with many patients who were previously on the drug "metformin" being able to switch with efficacy to 100 mg of enol-oxaloacetic acid and 100 mg of ascorbic acid in a once-per-day oral formulation.

The amount of the CR mimetic OAA to use is dependent upon the condition. Metabolic syndrome and diabetes are effectively treated with 100 to 1,000 mg enol-oxaloacetic acid in dry form per day, and more preferably 100 to 300 mg per day. Such an amount will activate AMPK. The dry powder can be kept from moisture accumulation by sealing the bottle and using a moisture absorbent such as silicone dioxide. For convenience, the dry powder should be placed in edible capsules or compressed into a pill. Alternately, a salt of oxaloacetic acid can also be used to activate AMPK and treat diabetes; however the salt must either be made up daily just prior to use, or part of a biphasic delivery system described earlier in this application. 100 to 1,000 mg Na-Oxaloacetate is effective in activating AMPK and treating diabetes. Other mono-valent and tri-valent oxaloacetate salts can also be used to activate AMPK, including, but not limited to, potassium oxaloacetate and chromium oxaloacetate. Delivery of these salts would be in the same manner and dosage as sodium oxaloacetate.

AMPK activation has been associated with reduced cancer incidence and metastasis. This is seen with the calorie restriction mimetic and AMPK activator metformin in meta studies, as well as specific studies with pancreatic and breast cancer cells (Zhuang, Y, et al, Cell cycle arrest in metformin treated breast cancer cells involves activation of AMPK, downregulation of cyclin D1, and requires p27Kip1 or p21Cip1, Journal of Molecular Signaling, (2008)1;3(1):18) (Wang, et. al., Metformin induces apoptosis of pancreatic cancer cells, World Journal of Gastroenterology, 2008, 21:14 (47):7192-8.) Calorie Restriction does not prevent cancer, rather, it retards the growth and metastasis of cancer. In a similar manner, the calorie restriction mimetic OAA inhibits cancer from reproducing and spreading. uM levels of oxaloacetate in contact with human A549 lung cancer tissue in vitro resulted in differential massive debris within the cancer tissue, but not within normal tissue. The massive debris resulted in the inability of the cancer tissue to reproduce, even if the cancer tissue was moved away from the oxaloacetate solution for a period of six weeks (Farah, et al Differential modulation of intracellular energetics in A549 and MRC-5 cells, Biomed Sci Instrum 2007 Volume 43, pp 110-5). Farah uses a contact solution of 76 uM, which can be delivered intravenously or orally. If orally, the concentration of OAA must be increased to 1,000 to 3,000 mg per day, preferably 500 to 700 mg with three meals during the day. Large volumes of OAA prevent the decay of the enzyme hypoxia inducible factor 1 (HIF-1), which leads to increased angiogenesis, which is undesirable in treating cancer (Lu, H, et. al., Reversible Inacivation of HIF-1 prolyl hydroxylases allows cell metabolism to control basal HIF-1. Journal of Biological Chemistry, 2005 280(51):41928-39). In order to prevent HIF-1 from inducing blood vessel formation where it is not needed, ascorbic acid (vitamin C) should be co-administered to the patient with the oxaloacetic acid. The amount of vitamin C supplemented to the patient can vary from as little as 100 mg upwards to 3,000 mg. Excess Vitamin C is excreted. The combination of Vitamin C and oxaloacetic acid is important because the oxaloacetic acid prevents the reproduction of the cancerous cells, whereas the addition of vitamin C prevents the oxaloacetic acid from stimulating blood vessel formation in existing tumors. While activation of AMPK is required to prevent cell cycling, and the growth and spread of solid tumors, the low cytotoxicity of OAA does little to kill the existing cells. Thus, in addition to vitamin C, OAA may be combined with other chemotherapies in order to destroy existing cancer cells. Optionally, the method can include the administration of a chemotherapeutic agent such as cyclophosphamide, chlorambucil, melphalan, estramustine, iphosphamide, prednimustin, busulphan, tiottepa, carmustin, lomustine, methotrexate, azathioprine, mercaptopurine, thioguanine, cytarabine, fluorouracil, vinblastine, vincristine, vindesine, etoposide, teniposide, dactinomucin, doxorubin, dunorubicine, epirubicine, bleomycin, nitomycin, cisplatin, carboplatin, procarbazine, amacrine, mitoxantron, tamoxifen, nilutamid, or aminoglutemide. The compound can be administered orally, topically, or parenterally. In some aspects of the invention, the chemotherapeutic agent is administered prior to administering the oxaloacetate compound. In other aspects, the chemotherapeutic agent is administered after or substantially contemporaneously with administering the compound. The cancer can be primary or metastatic malignant solid tumor disease or a hematological malignancy. If the cancer is a hematological malignancy, it may include acute and chronic myelogenous leukemia, acute and chronic lymphatic leukemia, multiple myeloma, Waldenstrom's macroglobulinemia, hairy cell leukemia, myelodisplastic syndrome, polycytaemia vera, and essential thrombocytosis.

AMPK activation has been associated with reduced Alzheimer risk and potentially with Alzheimer's treatment (Richter, Erik and Ruderman, Neil, "AMPK and the biochemistry of exercise: implications for human health and disease" Biochem. J. (2009) 418, 261-275). Thus OAA may be used for reducing the risk of Alzheimer's disease and for treatment of the same. A major advantage of using OAA for neurological diseases is that OAA can penetrate the blood-brain barrier.

Pharmaceutical Compositions

Pharmaceutical Preparations and Methods of Administration

Oxaloacetate can be administered to an individual at therapeutically effective doses for the prevention or treatment of disorders such as diabetes, metabolic syndrome, obesity, body weight disorders cardiovascular disease, Alzheimer's disease, and cancer.

As used herein, "oxaloacetate or OAA" includes oxaloacetic acid, the salt of the acid, or oxaloacetate in a buffered solution as well as mixtures thereof. The term similarly includes oxaloacetate precursors such as alpha-ketoglutarate and aspartate.

Effective Dose

A therapeutically effective dose refers to that amount of oxaloacetate sufficient to result in the desired effect such as the amelioration of symptoms relating to diabetes, metabolic syndrome, obesity, body weight disorders cardiovascular disease, Alzheimer's disease, and cancer.

Toxicity and therapeutic efficacy of oxaloacetate can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50 /ED50. The LD50 of alpha-ketoglutarate for mice is above 5 g/kg of body weight. The LD50 of oxaloacetate is above 5 g/kg of body weight. The "no observable adverse effects level" (NOAEL) in a 90-day sub-chronic rat study was 500 mg/kg (the highest dose in the test). Oxaloacetate has a very low toxicity, as would be expected from a chemical involved in the Citric Acid Cycle of every cell.

Toxicity studies of oxaloacetate run in Japan in 1968 on rats indicates that levels of oxaloacetate at 83 mg/kg of body weight caused changes in pancreatic islets. Some islets were decreased in size and hyperemic, alpha cells being atrophic, while beta cells were hypertrophic and stained densely. At lower doses, 41 mg/kg of body weight, the pancreas of the rates only demonstrated proliferation and hyperplasia of the islet cells. The liver, hypophysis, adrenals and gonadal glands showed no particular changes (Yoshikawa, Anti-diabetic effect of sodium oxaloacetate, 1968 Tohoku Journal of Experimental Medicine).

In clinical studies examining the effect of oxaloacetate on diabetes in humans, 21 diabetic patients received 100 mg to 1,000 mg (2-10 mg/kg of body weight). There were no negative side effects. Blood glucose levels dropped significantly in all patents and urine glucose levels dropped in 19 out of the 21 patents (Yoshikawa, Anti-diabetic effect of sodium oxaloacetate, 1968 Tohoku Journal of Experimental Medicine).

An example of an effective dose of oxaloacetate administered by an intravenous injection is from between about 0.5 mg to about 1 g of oxaloacetate for each kg of body weight. In a preferred embodiment, the effective dose of oxaloacetate is between about 2.0 mg and about 40 mg for each kg of body weight. Due to the acidity of the compound, the effective dose can be administered in multiple injections over several hours, or continuously. Effective oral dosing would likewise range from about 0.5 mg to about 1 g of oxaloacetate for each kg of body weight with the preferred effective dosage range between about 2 mg to about 40 mg of oxaloacetate for each kg of body weight. For example, an adult male weighing approximately 80 kg would be administered between about 150 mg to about 3.5 g of oxaloacetate orally per day. Dermally, topical formulations comprising concentrations of about 0.5 to 16 mM of oxaloacetate are effective. CR studies indicate that restricting calories every-other-day yields the same beneficial results as daily CR. Similarly, in some embodiments, oxaloacetate is administered every-other-day, as once the genes are activated, the effect lasts for at least a two-day period of time. In other embodiments, oxaloacetate is administered 3 times per day after each meal.

Formulations

Pharmaceutical compositions for use in accordance with the present invention may be formulated in conventional manner using one or more physiologically acceptable carriers or excipients. Thus, oxaloacetate and its physiologically acceptable salts and solvates may be formulated for administration by inhalation or insufflation (either through the mouth or the nose) or oral, buccal, topical, transdermal, parenteral, or rectal administration. In the case of inhalation, the administration of oxaloacetate will provide aging benefits directly to lung tissue, even if the dosage of oxaloacetate administered is less than is needed to benefit the entire organism. Inhalation of oxaloacetate will delay the on-set of age-related diseases of the lungs and will provide protection from lung diseases.

Oxaloacetate is acidic. The acidity is unlikely to affect organisms that ingest the compound in beneficial amounts as the interior conditions of the stomach are also very acidic. The acidity may affect other tissues, including but not limited to the skin or lungs, that may benefit from the direct application of oxaloacetate. Therefore, in another embodiment, a composition of matter can be created by mixing oxaloacetate with a buffer solution or a base or used as a salt of oxaloacetate so the delivered compound is not caustic. This will enable higher concentrations of oxaloacetate to be delivered safely to the organism, especially if the oxaloacetate is not delivered by oral ingestion.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, non-water solutions, syrups or suspensions, or they may be presented as a dry product for constitution with water or other suitable vehicle immediately before use (due to decarboxylation concerns). Water acts as a catalyst which allows for the conversion of solid enol-oxaloacetate to convert to the liquid keto-oxaloacetate form which spontaneously decarboxylates into pyruvate and carbon dioxide. Such non-water liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

While the absorption of oxaloacetate from the digestive tract will increase the entire organism's oxaloacetate levels, the immediate contact of oxaloacetate to the cells in the digestive tract will preferentially be in contact with the digestive tract cells, allowing the reduction in gastric diseases such as colon cancer, even if the ingested amounts of oxaloacetate are insufficient to provide benefit to the entire organism.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

A topical application is the preferred method of administration of oxaloacetate for increasing the activity of AMPK directly at the dermis for the treatment or prevention of skin cancer. The topical pharmaceutical and cosmetic compositions of the present invention maybe made into a wide variety of product types. These include, but are not limited to lotions, creams, beach oils, gels, sticks, sprays, ointments, pastes, mousses and cosmetics. These product types may comprise several types of pharmaceutical or cosmetic carrier systems including, but not limited to solutions, emulsions, gels and solids. The topical pharmaceutical and cosmetic compositions of the present invention formulated as solutions typically include a pharmaceutically-acceptable organic solvent. The terms "pharmaceutically-acceptable organic solvent" refer to a solvent which is capable of having dissolved therein the oxaloacetate, and possesses acceptable safety properties (e.g., irritation and sensitization characteristics). Examples of a suitable pharmaceutically acceptable organic solvent include, for example, monohydric alcohols, such as ethanol, and polyhydric alcohols, such as glycols. If the topical pharmaceutical and cosmetic compositions of the present disclosure are formulated as an aerosol and applied to the skin as a spray-on, a propellant is added to a solution composition.

A type of product that may be formulated from a solution carrier system is a cream or ointment. An ointment can comprise a simple base of animal or vegetable oils or semi-solid hydrocarbons (oleaginous). An ointment can include from about 0.1% to about 2% of a thickening agent. Examples of suitable thickening agents include: cellulose derivatives (e.g., methyl cellulose and hydroxy propylmethylcellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers (CARBOPOLS®; sold by B. F. Goodrich Company, such polymers are described in detail in Brown, U.S. Pat. No. 2,798,053, issued Jul. 2, 1975). A more complete disclosure of thickening agents useful herein can be found in Sagarin, Cosmetics, Science and Technology, 2nd Edition, Vol. 1, pp.72-73 (1972). If the carrier is formulated as an emulsion, from about 1% to about 10%, for instance, from about 2% to about 5%, of the carrier system comprises an emulsifier. Suitable emulsifiers include nonionic, anionic or cationic emulsifiers. Exemplary emulsifiers are disclosed in, for example, McCutcheon's Detergents and Emulsifiers, North American Edition, pages 317-324 (1986). Preferred emulsifiers are anionic or nonionic, although other types can also be employed.

An emulsion carrier system useful in the topical pharmaceutical and cosmetic compositions of the present disclosure is a microemulsion carrier system. Such a system preferably comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with the therapeutic agents described above, with the oxaloacetate carried in the non-water portion.

The topical pharmaceutical and cosmetic compositions of the present disclosure can also include a safe and effective amount of a penetration enhancing agent. Other conventional skin care product additives may also be included in the compositions of the present invention. For example, collagen, elastin, hydrolysates, primrose oil, jojoba oil, epidermal growth factor, soybean saponins, mucopolysaccharides, and mixtures thereof may be used. Various vitamins can also be included in the compositions of the present invention. For example, Vitamin A, and derivatives thereof, Vitamin B2, biotin, pantothenic, Vitamin D, and mixtures thereof can be used.

In yet a further embodiment of the current invention, the oxaloacetate delivered topically can be mixed with a penetration enhancing agent such as dimethylsulfoxide (DMSO), combinations of sucrose fatty acid esters with a sulfoxide or phosphoric oxide, or eugenol, that allows faster migration of the oxaloacetate into the dermal tissues and then further into deeper cellular tissues, including cellulite tissues where stimulation of the Sirt1 gene will cause a reduction of fat tissues.

In one embodiment, the disclosed compounds are administered through a topical delivery system. Implantable or injectable polymer matrices, and transdermal formulations, from which active ingredients are slowly released are also well known and can be used in the disclosed methods. The controlled release components described above can be used as the means to delivery the disclosed compounds. The compositions can further include components adapted to improve the stability or effectiveness of the applied formulation, such as preservatives, antioxidants, skin penetration enhancers and sustained release materials. Examples of such components are described in the following reference works hereby incorporated by reference: Martindale—The Extra Pharmacopoeia (Pharmaceutical Press, London 1993) and Martin (ed.), Remington's Pharmaceutical Sciences.

Controlled release preparations can be achieved by the use of polymers to complex or absorb oxaloacetate. The controlled delivery can be exercised by selecting appropriate macromolecule such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active compound.

In another embodiment, transdermal patches, steady state reservoirs sandwiched between an impervious backing and a membrane face, and transdermal formulations, can also be used to deliver oxaloacetate. Transdermal administration systems are well known in the art. Occlusive transdermal patches for the administration of an active agent to the skin or mucosa are described in U.S. Pat. Nos. 4,573,996, 4,597, 961 and 4,839,174, which are hereby incorporated by reference. One type of transdermal patch is a polymer matrix in which the active agent is dissolved in a polymer matrix through which the active ingredient diffuses to the skin. Such transdermal patches are disclosed in U.S. Pat. Nos. 4,839,174, 4,908,213 and 4,943,435, which are hereby incorporated by reference. In one embodiment, the steady state reservoir carries doses of oxaloacetate in doses from about 2 mg to 40 mg per day.

Present transdermal patch systems are designed to deliver smaller doses over longer periods of time, up to days and weeks. A rate-controlling outer microporous membrane, or micropockets of the disclosed oxaloacetate dispersed throughout a silicone polymer matrix, can be used to control the release rate. Such rate-controlling means are described in U.S. Pat. No. 5,676,969, which is hereby incorporated by reference. In another embodiment, the oxaloacetate is released from the patch into the skin of the patient in about 20-30 minutes or less.

These transdermal patches and formulations can be used with or without use of a penetration enhancer such as dimethylsulfoxide (DMSO), combinations of sucrose fatty acid esters with a sulfoxide or phosphoric oxide, or eugenol. The use of electrolytic transdermal patches is also within the scope of the methods disclosed herein. Electrolytic transdermal patches are described in U.S. Pat. Nos. 5,474,527, 5,336,168, and 5,328,454, the entire contents of which are hereby incorporated by reference.

Oxaloacetate may be formulated for parenteral administration by injection, e.g., by bolus injection or continuous infusion. The injected oxaloacetate can be mixed with other beneficial agents prior to injection including but not limited to antibiotics and other medications, saline solutions, blood plasma, and other fluids. Immediate contact of elevated levels of oxaloacetate with the vascular system cells will result in the reduction in age-related diseases such as hardening of the arteries, even if the amounts of oxaloacetate are insufficient to provide age-related benefits to the entire organism. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before immediate use.

Oxaloacetate may also be formulated in rectal compositions such as suppositories or retention enemas, e.g., containing conventional suppository bases such as cocoa butter or other glycerides.

In addition to the formulations described previously, oxaloacetate may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

In yet still another embodiment, oxaloacetate can be mixed with animal foods for the prevention or treatment of disorders such as diabetes, metabolic syndrome, obesity, cardiovascular disease, Alzheimer's disease, and cancer in animals. Oxaloacetate can either be formulated as part of the animal food or administered separately as a supplement to the animal's food. As those skilled in the art know, dry pet foods, typically dry dog foods, normally contain protein, fat, fiber, non-fiber carbohydrates, minerals, vitamins and moisture components. For example, as major ingredients, there are typically one or two cereal grains, generally corn, wheat and/or rice. In addition, for a protein source they may contain poultry meal, by-product meat, meat and bone meal, or other animal or fish meal by-products. At times as well, grain protein supplements such as corn gluten, soybean meal or other oil seed meals can be added. In addition to an effective amount of oxaloacetate of between about 0.01% to 0.1% by weight of the chow, animal chow of the present invention additionally includes the following: typical nutrient content in the food dry matter includes crude protein from 14% to 50%, usually 20% to 25%; crude fat from 5% to 25%; and crude fiber usually is present in the range of from about 3% to 14%, usually about 5% to 7%, with the total mineral or ash content being within the range of 3% to 10%, usually 4% to 7%. The important point is not the precise formulation of the pet food, since many conventional and satisfactory ones for use in conjunction with the present invention are available on the market. Rather, the key to success is that a sufficient amount of oxaloacetate component be added to pet food rations, whichever formulation is used, to provide the oxaloacetate activity level at the ranges necessary for AMPK activation in order to support the prevention or treatment of disorders such as diabetes, metabolic syndrome, obesity, cardiovascular disease, Alzheimer's disease, and cancer in animals.

Uses and Indications

Based on the inventors' findings (see examples below) and other data in the literature that relate to the benefits of AMPK activation referenced herein, it is contemplated that the compounds and pharmaceutical compositions presented herein are used as prophylactic and/or therapeutic agents for various conditions, and particularly in the prevention and/or treatment of metabolic syndrome, pre-diabetes, insulin resistance, type 2 diabetes, and/or dyslipidemia. It should be appreciated that the term "treated" or "treatment" where used in conjunction with a medical condition refers to at least one of a resolution and/or improvement in clinical parameters of clinically abnormal values, and/or to an improvement in subjective feeling of a patient diagnosed with the condition.

Viewed from another perspective, it is also contemplated that various benefits may be derived from administration of the compounds and pharmaceutical compositions presented herein, and especially contemplated benefits relate to prevention, amelioration, and/or treatment of diseases or conditions associated with activation of AMPK, and the following provides exemplary guidance on contemplated benefits.

Hyperglycemia

It has recently been reported that therapeutic doses of metformin increase AMPK activity in vivo in subjects with type 2 diabetes (Diabetes, 51(7): 2074-81, 2002). Metformin treatment for 10 weeks significantly increased AMPK alpha 2 activity in the skeletal muscle, and this was associated with increased phosphorylation of AMPK on Thr172 and decreased acetyl-CoA carboxylase-2 activity. The increase in AMPK alpha 2 activity was likely due to a change in muscle energy status because ATP and phosphocreatine concentrations were lower after metformin treatment. Metformin-induced increases in AMPK activity were associated with higher rates of glucose disposal and muscle glycogen concentrations. These findings suggest that the metabolic effects of metformin in subjects with type 2 diabetes may be mediated by the activation of AMPK alpha 2. Given the hypoglycemic effect imparted by the activation of AMPK, administration of contemplated pharmaceutical products to increase AMPK activity may be useful to lower blood glucose concentrations by decreasing hepatic glucose production and increasing glucose disposal in skeletal muscle.

Athletic Performance

AMPK activation leads to PGC-1alpha activation which leads to mitochondrial biosynthesis (Lopez-Lluch, et al. Mitochondrial Biogenesis and Healthy Aging, Expermental Gerontology, 2009 September; 43(9):813-819.doi:10.1016/j.exger.2008.06.014.) Increasing mitochondrial biosynthesis will lead to increased mitochondrial density in the muscle cells. Increased mitochondrial density will increase athletic performance in terms of muscle strength and endurance.

Reduced Insulin Sensitivity

Conditions and disorders associated with diminished insulin sensitivity of muscle glucose transport may be treated by administration of contemplated compounds. Various reports suggest that increase in insulin sensitivity of muscle glucose transport following exercise is mediated by activation of AMPK. Thus, ingestion of contemplated pharmaceutical products is thought to provide increased insulin sensitivity of muscle glucose transport.

Insulin Resistance Syndrome

Insulin resistance syndrome is associated with obesity, type 2 diabetes, and muscle paralysis (see e.g., WO 01/97816 A1 and WO 01/93874 A1). Insulin resistance syndrome is also associated with several risk factors for cardiovascular disease. In view of numerous papers suggesting that activating AMPK improves glucose tolerance, improves the lipid profile, and reduces systolic blood pressure, ingestion of contemplated pharmaceutical products to increase AMPK activity is deemed useful to reduce metabolic disturbances and/or to lower blood pressure characteristic of insulin resistance syndrome.

Insufficient Glucose Uptake in Muscle Cells

It has been observed that exercise and/or electrical stimulation of various muscles increases AMPK activity, and consequently increases glucose uptake. Based on these observations, it has been hypothesized that muscle contraction plays a role in stimulating glucose uptake in muscle, where one mechanism underlying increased uptake stems from activated AMPK increasing GLUT-4 translocation from microvesicles to sarcolemmal membranes in muscle.

Based on the inventors' observation that compounds with cytokinin activity increase AMPK activity, it should be recognized that contemplated pharmaceutical products may be beneficial in enhancing glucose uptake into muscle cells (as well as being beneficial in ameliorating disorders that are characterized by decreased glucose uptake in muscle cells, or that are exacerbated by the effects of decreased glucose uptake in muscle cells).

Insulin Oversecretion

It is generally accepted in the art that activated AMPK inhibits insulin secretion, and as contemplated compounds were demonstrated to activate AMPK, it should be recognized that treatment with such compounds should provide a significant reduction in insulin secretion. Consequently, conditions associated with oversecretion of insulin may benefit from ingestion of contemplated pharmaceutical products.

Dyslipidemia

Hepatic acetyl-CoA carboxylase (ACC) and 3-hydroxy-3-methylglutaryl-CoA reductase (HMGR) are two targets for the AMPK system, catalyzing the key regulatory steps in fatty acid and sterol synthesis, respectively (Winder et al, Am J Physiol, 2777: E1-10, 1999, the entirety of which is herein incorporated by reference.) Activation of AMPK serves to inhibit both these lipid biosynthetic pathways, as well as triglyceride synthesis. Moreover, it is contemplated that activated AMPK inhibits the L-type pyruvate kinase and fatty acid synthase gene expression.

Reduction of activity of ACC in the liver cell also leads to decreases in the concentration of the product of ACC, i.e., malonyl-CoA, which has marked effects on fatty acid oxidation. Malonyl-CoA is a potent inhibitor of carnitine palmitoyltransferase-1 (CPT-1), the "gatekeeper" for entry of fatty acids into the mitochondria. In the liver, fatty acid oxidation can be considered to be an essential component of the pathway for synthesis of ketone bodies: increases in fatty acid oxidation lead to increased hepatic ketogenesis. It is therefore contemplated that administration of contemplated compounds at a concentration effective to activate AMPK in the liver would result in decreases in fatty acid, triglyceride, and sterol synthesis and increases in fatty acid oxidation and ketogenesis. Viewed from another perspective, contemplated pharmaceutical products may be useful to increase AMPK activity and thereby reduce fatty acid synthesis, sterol synthesis, triglyceride synthesis and fatty acid synthase gene expression. Of additional benefit is also the AMPK-mediated increase in activity in fatty acid oxidation and ketogenesis, where increased ketogenesis is desired.

Obesity

Hormone-sensitive lipase (HSL) is a target for AMPK in adipose tissue. Activation of AMPK has been shown to inhibit lipogenesis by phosphorylation of ACC and also to inhibit isoprenaline-stimulated lipolysis. Thus, contemplated pharmaceutical products may help reduce or even abolish lipogenesis and/or increase isoprenaline-stimulated lipolysis. Thus, and given the inhibitory role for AMPK in the process of adipose differentiation, it should be recognized that contemplated pharmaceutical products will likely inhibit adipogenesis.

Reduction in Fat accumulation after dieting

Activation of AMPK has been shown to inhibit lipogenesis, which is increased after ending a diet. The increase in lipogenesis leads to rapid increases in weight, often referred to as the "diet rebound effect". This rebound effect can be reduced or eliminated with OAA supplementation.

Modulation of Stability of Selected mRNA Species

HuR is an RNA binding protein that functions to stabilize a variety of target mRNA transcripts, including those encoding p21, cyclinA and cyclinB1. It has been shown that the presence of activated AMPK results in reduced levels of cytoplasmic HuR, and in turn, in reduced concentrations and half-lives of mRNA encoding p21, cyclinA and cyclinB1 (see e.g., Mol Cell Biol, 22(10):345-36, 20002, which is incorporated herein by reference). Thus, treatment with contemplated compounds will increase AMPK activity, and thus reduce levels of cytoplasmic HuR, which is thought to reduce concentrations/half-lives of a variety of target mRNA transcripts, including those ending p21, cyclinA and cyclinB1.

Premature Apoptosis

Activated AMPK has been shown to provide protection against glucocorticoid-induced apoptosis and to restore cell viability and inhibit DNA laddering in dexamethasone-treated thymocytes (see e.g., Biochem Biophys Res Commun, 243(3):821-6, 1998, which is incorporated herein by reference). Furthermore, activated AMPK has been shown to provide protection against dexamethasone-induced activation of caspase 3-like enzymes, which are believed to play a pivotal role in apoptotic cell death. Thus, treatment with contemplated compounds to increase AMPK activity may provide protection against glucocorticoid-induced apoptosis.

Ischemia

Conditions and disorders associated with AMPK regulation of cellular responses to stresses, including ischemia, are among those treatable by administering a composition comprising a compound that activates AMPK. In several non-vascular tissues, AMPK appears to modulate the cellular response to stresses such as ischemia. In liver and muscle, AMPK phosphorylates and inhibits acetyl CoA carboxylase (ACC), leading to an increase in fatty acid oxidation; in muscle, AMPK activation is associated with an increase in glucose transport. Furthermore, incubation of human umbilical vein endothelial cells (HUVEC) with an AMPK activator has been shown to cause a 5-fold activation of AMPK, which was accompanied by a 70% decrease in ACC activity and a 2-fold increase in fatty acid oxidation. (Biochem Biophys Res Commun, 265(1):112-5, 1999, which is incorporated herein by reference). However, in this same study, glucose uptake and glycolysis, the dominant energy-producing pathway in HUVEC, were diminished by 40-60% under these conditions. Despite this, cellular ATP levels were increased by 35%. Thus, treatment with contemplated compounds to increase AMPK activity is expected to result in major alterations in endothelial cell energy balance, which are useful in providing protection against cellular stresses in conditions including ischemia.

Metabolic and Excitotoxic Insults

It is well known in the art that the brain has a high metabolic rate and is relatively sensitive to changes in the supply of glucose and oxygen. The expression of AMPK in embryonic and adult brain and its role in modifying neuronal survival under conditions of cellular stress have been investigated (J Mol Neurosci, 17(1): 45-58, 2001). Catalytic (alpha 1 and alpha 2) and noncatalytic (beta 2 and gamma 1) subunits of AMPK are present at high levels in embryonic hippocampal neurons in vivo and in cell culture. In the adult brain, the catalytic subunits alpha 1 and alpha 2 are present in neurons throughout the brain. The AMPK-activating agent AICAR protected hippocampal neurons against death induced by glucose deprivation, chemical hypoxia, and exposure to glutamate and amyloid beta-peptide. Suppression of levels of the AMPK alpha 1 and alpha 2 subunits using antisense technology resulted in enhanced neuronal death following glucose deprivation, and abolished the neuroprotective effect of AICAR. Thus, given the role of AMPK activation in modifying neuronal survival under conditions of cellular stress, treatment with contemplated compounds to increase AMPK activity is thought to provide protection of neurons against metabolic and excitotoxic insults.

Similarly, conditions and disorders associated with hypoxia may be treated using contemplated compounds. AMPK is believed to play a role in regulating ketone body production by astrocytes. (J Neurochem, 73(4): 1674-82, 1999). Incubation of astrocytes with AICAR has been shown to stimulate both ketogenesis from palmitate and carnitine palmitoyltransferase I concomitant to a decrease of intracellular malonyl-CoA levels and an inhibition of acetyl-CoA carboxylase/fatty acid synthesis and 3-hydroxy-3-methyl-glutaryl-CoA reductase/cholesterol synthesis. Moreover, microdialysis experiments have shown AICAR to stimulate brain ketogenesis markedly. Incubation of astrocytes with azide has been shown to lead to a remarkable drop of fatty acid beta-oxidation. However, activation of AMPK during hypoxia was shown to compensate the depression of beta-oxidation, thereby sustaining ketone body production. The effect is believed to rely on the following cascade: hypoxia leads to an increase of the AMP/ATP ratio, which triggers AMPK stimulation, which in turn results in acetyl-CoA carboxylase inhibition. Consequently, malonyl-CoA concentration decreasesm and carnitine palmitoyltransferase I is activated, thus enhancing ketogenesis. Furthermore, incubation of neurons with azide has been shown to blunt lactate oxidation, but not 3-hydroxybutyrate oxidation. Thus, given the role of AMPK activation in regulating ketone body production by astrocytes, treatment with contemplated compounds to increase AMPK activity is useful in promoting astrocytes to produce ketone bodies as a substrate for neuronal oxidative metabolism during hypoxia.

Hepatic Ischemia-Reperfusion

Hepatic ischemia-reperfusion (I/R) injury associated with liver transplantation and hepatic resections may be reduced by administering a composition comprising a compound that activates AMPK. Preconditioning is known to preserve energy metabolism in liver during sustained ischemia. A study has been reported that investigates: 1) whether preconditioning induces AMPK activation; and 2) if AMPK activation leads to ATP preservation and reduced lactate accumulation during prolonged ischemia and its relationship with NO (Hepatology, 34(6): 1164-73, 2001). Preconditioning was reported to activate AMPK and concomitantly reduce ATP degradation, lactate accumulation, and hepatic injury. The administration of an AMPK activator, AICAR, before ischemia simulated the benefits of preconditioning on energy metabolism and hepatic injury. The inhibition of AMPK abolished the protective effects of preconditioning. The effect of AMPK on energy metabolism was independent of NO because the inhibition of NO synthesis in the preconditioned group and the administration of the NO donor before ischemia, or to the preconditioned group with previous inhibition of AMPK, had no effect on energy metabolism. Thus, given the role of AMPK activation in the protective effect against ischemia, treatment with contemplated compounds to increase AMPK activity is contemplated for surgical and pharmacological strategies aimed at reducing hepatic I/R injury.

It is well established that nutrient deprivation activates AMPK (supra), and that tumors in a relatively early stage are dependent on nutrient diffusion. Thus, when a tumor reaches a critical mass, AMPK will be activated in at least some cells due to lack of glucose and other growth factors. Consequently, the inventors contemplate that contemplated anti-cytokinins may be employed to block energy salvage pathways of tumor cells (see e.g., Oncogene. 2002 Sep. 5; 21(39):6082-90: Critical roles of AMP-activated protein kinase in constitutive tolerance of cancer cells to nutrient deprivation and tumor formation by Kato et al.).

Therefore, it should be appreciated that contemplated pharmaceutical compositions and contemplated compounds may especially beneficial to a person to (1) reduce fatty acid synthesis, sterol synthesis, triglyceride synthesis and fatty acid synthase gene expression, (2) ameliorate one or more conditions or disorders that are characterized by elevations in one or more of the pathways or mechanisms involved in fatty acid synthesis, sterol synthesis, triglyceride synthesis and fatty acid synthase gene expression, (3) increase fatty acid oxidation and ketogenesis, (4) inhibit lipogenesis and/or isoprenaline-stimulated lipolysis, (5) ameliorate one or more conditions or disorders that are characterized by elevations in one or both of lipogenesis and isoprenaline-stimulated lipolysis pathways, or that are exacerbated by the elevations in one or both of these pathways, (6) decrease insulin secretion, (7) ameliorate one or more a conditions or disorders that are characterized by elevated insulin secretion, or that are exacerbated by insulin secretion, (8) enhance glucose uptake in muscle cells, (9) ameliorate one or more conditions or disorders that are characterized by decreased glucose uptake in muscle cells, or that are exacerbated by the effects of decreased glucose uptake in muscle cells, (10) inhibit adipogenesis, (11) ameliorate one or more conditions or disorders that are characterized by increased adipogenesis, or that are exacerbated by adipogenesis, (12) increase insulin sensitivity of muscle glucose transport, (13) lower blood glucose concentrations by decreasing hepatic glucose production and/or increasing glucose disposal in skeletal muscle, and/or (14) ameliorate one or more conditions or disorders associated with insulin resistance syndrome through improving glucose tolerance, improving lipid profile or reducing systolic blood pressure.

It should be especially appreciated that traditional long term metformin therapy often requires concurrent supplementation with calcium carbonate to prevent the adverse impact of metformin administration on vitamin B 12 absorption. It has been postulated that the hydrophobic tail of biguanides, such as metformin, extends into the hydrophobic core of membranes, thereby adding a positive charge to the surface of the membrane, which acts to displace divalent cations (see e.g., Bauman et al. (Diabetes Care 2000; 23:1227-31)), which in turn negatively affects binding of the B 12-intrinsic factor complex to the ileal cell surface receptors. Such adverse consequences are not expected using OAA as they are significantly structurally different from biguanides.

Consequently, the inventor contemplates a method of modulating glucose metabolism in a mammal in which in one step a contemplated compound/pharmaceutical composition is administered to a the mammal at a dosage effective to modulate glucose metabolism in the mammal. In especially contemplated aspects, the mammal is a human and diagnosed with metabolic syndrome, pre-diabetes, insulin resistance, type-2 diabetes, and/or dyslipidemia. Additionally, or alternatively, contemplated compounds/pharmaceutical compositions may also be prophylactically administered to prevent or delay onset or progression of metabolic syndrome, pre-diabetes, insulin resistance, type-2 diabetes, and/or dyslipidemia. While not limiting to the inventive subject matter, the inventors contemplate that such treatment may be due to an increase in glucose uptake into a muscle cell (or other cell), and/or due to a decrease in gluconeogenesis in a hepatocyte. With respect to the hepatocyte, and while not limiting to the inventive subject matter, the inventors contemplate that the compounds presented herein will directly or indirectly affect activity of the glucocorticoid receptor, PEPCK (phosphoenolpyruvate carboxykinase), the glucagon receptor, and/or glucose-6-phosphatase. From a genomic standpoint, activation of AMPK also increases the expression of the FOXO3a gene, associated with increasing glucose homeostasis.

Similarly, in further preferred aspects, the inventors contemplate a method of modulating lipid metabolism in a mammal in which in one step a contemplated compound/pharmaceutical composition is administered to a the mammal at a dosage effective to modulate glucose metabolism in the mammal. Such methods may advantageously be employed to treat or prevent metabolic syndrome and/or dyslipidemia, and may also be employed to decrease at least one of total serum cholesterol, serum LDL-cholesterol, and serum triglycerides.

Viewed from another perspective, the inventors also contemplate a method of treating a condition in a mammal, wherein the condition is associated with a dysregulation of at least one of AMPK. In such methods, a contemplated compound/pharmaceutical composition is administered to the mammal at a dosage effective to activate AMPK. Among other conditions, especially contemplated conditions for such methods include cardiovascular disease, type 2 diabetes, Alzheimer's disease and a neoplastic disease.

EXAMPLES

Example 1

A non-diabetic subject is given 100 mg anhydrous enol-oxaloacetic acid in solid form for a period of 6 months to reduce blood triglycerides and glucose levels. AMPK is activated and the treatment is effective.

|  | Feb-07 | Aug-07 | % Change |  |
|---|---|---|---|---|
| Glucose Fasting (mg/dl) | 97 | 89 | 8.25% | Decrease (Improvement) |
| Lipid Panel |  |  |  |  |
| Triglyceride (mg/dl) | 112 | 102 | 8.93% | Decrease (Improvement) |
| Total Cholesterol (mg/dl) | 202 | 203 |  |  |
| HDL Ser Cholesterol (mg/dl) | 42 | 42 |  |  |
| LDL Cholesterol (mg/dl) | 138 | 138 |  |  |
| Glomeruler Filtration Rate (GFR) |  |  |  |  |
| Bun-Ser (mg/dl) | 14 | 12 |  |  |
| Albumin (g/dl) | 4.4 | 4.2 |  |  |
| Creatinine (mg/dl) | 1 | 0.9 |  |  |
| Electrolyte Panel |  |  |  |  |
| Na (Sodium) (mEq/L) | 144 | 143 |  |  |
| Cl (Chloride) (mEq/L) | 110 | 108 |  |  |
| K (Potassium) (mEq/L) | 4.6 | 4.5 |  |  |
| CO2 (Carbon Dioxide) (mEq/L) | 27 | 29 |  |  |
| ALK P'TASE (IU/L) | 36 | 37 |  |  |
| AST (SGOT) (IU/L) | 16 | 15 |  |  |
| TSH (uIU/ml) | 1.41 | 1.32 |  |  |
| Lipase (u/l) | 17 | 19 |  |  |

Example 2

A patient is given 100 mg anhydrous enol-oxaloacetic acid daily in solid form and blood glucose levels are tracked for several weeks. The amplitude of the patient's swings in fasting glucose decrease by 55% due to improved glucose homeostasis. AMPK is activated and overall fasting glucose levels drop by 8%. The data is shown in Graph 3.

Example 3

A patient is given 100 mg anhydrous enol-oxaloacetate daily in solid form and continues with his normal routine. AMPK is activated and the patient drops in weight from 258 to 234 pounds in a three month period. The patient is no longer obese.

| Starting Weight Feb 2007 | Ending Weight May 2007 | Percent Reduction |
|---|---|---|
| 258 | 234 | 9.3% |

Example 4

A patient successfully loses 24 pounds. In order to maintain the weight loss, the patient is given 100 mg anhydrous enol-oxaloacetic acid daily in solid form. AMPK is activated which down regulates human homologues of the following genes in the liver; Acaal, Cnbp, Fasn, Idil, Ndufabl, Pcx, Sc5d, all of which reduces the body's ability to create and store fat. The patient does not regain the weight lost during a one-year period after the diet.

Example 5

A patient is diagnosed with hypertension. The patient is given 100 mg anhydrous enol-oxaloacetic acid daily in solid form for three months. The patient's blood pressure decreases by 10%.

Example 6

A patient has a family history of colon cancer. The patient is given 200 mg anhydrous enol-oxaloacetic acid and 200 mg Vitamin C in solid form in order to reduce the development of cancerous polyps into colon cancer. After a three year interval between colonoscopies, the incidence of pre-cancerous polyps is reduced by 50%, despite the increase in age of the patient and the typical correlation between increasing age and increasing polyp incidence.

Example 7

A patient is diagnosed with lung cancer. The patient is given 500 mg anhydrous enol-oxaloacetic acid with each meal along with 500 mg Vitamin C in solid form in addition to chemotherapy. The patient has a successful recovery from cancer. The patient is placed on a maintenance dose of 200 mg anhydrous enol-oxaloacetic acid and 200 mg Vitamin C per day to reduce risk of reoccurrence.

Example 7

A patient has a family history of Alzheimer's disease. The patient is administered 200 mg anhydrous enol-oxaloacetic acid and 200 mg Vitamin C per day to activate AMPK and delay incidence of Alzheimer's disease.

Example 8

Here I report a case study on a 73 year old Hungarian woman, weight of 89 kg, with a history of difficult to treat Type 2 diabetes. The trial was a "grass-roots" look at glucose levels performed by the patient with a glucose test strip meter under normal living conditions. The unsolicited data was supplied to us as the developer of the nutritional supplement product. Unfortunately, no other measurements were taken by the patient other than blood glucose levels, but the number of readings taken by the patient is impressive, and does show statistically significant results. At the start of the study, the woman was on the following medications:

Diaprel MR/(80 mg)-2 per day—Extended release Gliclazide (80 mg), a once per day diabetic drug
Pentoxyl-EP (400 mg)—1 per day—Contains pentoxifylline, used for intermittent Claudication (A symptom complex characterized by leg pain and weakness brought on by walking, with the disappearance of the symptoms following a brief rest).
Merckformin (1,000 mg)—1 per day—(Metformin, Glucophage)—used for Type 2 diabetes
Glycerine sol (0.5 dl) After dinner
Avandamet—1 per day—a combination of metformin and rosiglitazone used for diabetes Her fasting glucose levels fluctuated from the 8 to 11 mmol/L and glucose levels after a meal increased up to 12 mmol/L. In addition to her current medicines, the patient self started 100 mg/ day stabilized oxaloacetic acid with 100 mg/day Vitamin C (combined in 1 capsule). During the study the patient increased the use of combination to two capsules, then three capsules per day. By the end of the 70 day study the patient's fasting glucose levels had dropped to a range between 7 and 8 mmol/L, and glucose levels after a meal remained more consistent in the 7 to 8.5 mmol/L range, levels not achievable with the three prescription medications the patient was consuming. Using linear trend analysis, the patient's fasting glucose levels dropped 23% from the start of the test to the end of the test. Her glucose levels after a meal dropped 34.5%, indicating a major improvement in glucose management and glucose tolerance. Comparison of the various glucose levels in the first half of the trial versus the second half of the trail yields a p value of <0.001, indicating a very significant difference between the first half and second half of the trial.

The reduction in glucose levels occurred despite a reduction in the amount of Mercformin (Metformin, Glucophage) from 1,000 mg/day to 850 mg/day during the study. The patient also stopped using Pentoxyl-EP and glycerol by the end of the study. The data from this case study is shown as FIG. 1. Improvement in this patient's glucose levels and glucose tolerance with stabilized oxaloacetic acid, an over-the-counter dietary supplement, was shown to successfully support proper glucose functioning.

Example 9

AMPK activation is necessary to increase lifespan of C. elegans when exposed to 8 mM concentrations of oxaloacetate. The increase in lifespan averages approximately 25%, p<0.001. In C. elegans that contain a dysfunctional AMPK gene (dysfunctional in the aak-2 subunit), AMPK is not activated by oxaloacetate, and there is no increase in lifespan.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended claims and any equivalents thereof. Additionally, throughout this application, various publications have been referenced. The disclosures in these publications are incorporated herein by reference in order to more fully describe the state of the art.

The invention claimed is:

1. A composition comprising a therapeutically effective amount from about 100 mg to about 3,000 mg anhydrous enol-oxaloacetic acid.

2. The composition of claim 1, wherein the composition comprises less than about 2% water.

3. The composition of claim 2, wherein the composition further comprises from about 100 mg to about 1,000 mg vitamin C.

4. The composition of claim 1, wherein the composition comprises less than about 1% water.

5. The composition of claim 4, wherein the composition further comprises from about 100 mg to about 1,000 mg vitamin C.

6. The composition of claim 1, wherein the composition further comprises from about 100 mg to about 1,000 mg vitamin C.

7. The composition of claim 1, wherein the composition comprises from about 100 mg to about 300 mg anhydrous enol-oxaloacetic acid.

8. The composition of claim 7, wherein the composition comprises less than about 2% water.

9. The composition claim 8, wherein the composition further comprises from about 100 mg to about 1000 mg vitamin C.

10. The composition of claim 7, wherein the composition comprises less than about 1% water.

11. The composition of claim 10, wherein the composition further comprises from about 100 mg to about 1000 mg vitamin C.

12. The composition of claim 7, wherein the composition further comprises from about 100 mg to about 1000 mg vitamin C.

13. The composition of claim 7, wherein the composition comprises about 100 mg anhydrous enol-oxaloacetic acid.

14. The composition of claim 13, wherein the composition comprises less than about 2% water.

15. The composition of claim 14, wherein the composition further comprises from about 100 mg to about 1000 mg vitamin C.

16. The composition of claim 13, wherein the composition comprises less than about 1% water.

17. The composition of claim 16, wherein the composition further comprises from about 100 mg to about 1000 mg vitamin C.

18. The composition of any one of claim 13, wherein the composition further comprises from about 100 mg to about 1000 mg vitamin C.

19. The composition of claim 18, wherein the composition comprises about 100 mg vitamin C.

\* \* \* \* \*